United States Patent [19]

Klein et al.

[11] Patent Number: 5,475,127

[45] Date of Patent: Dec. 12, 1995

[54] ORGANOSILYL AND ORGANOSILOXANYL DERIVATIVES OF GLYCERIN ETHERS AND THEIR USE

[75] Inventors: Klaus-Dieter Klein, Mülheim; Wilfried Knott, Essen, both of Germany

[73] Assignee: Th. Goldschmidt AG, Essen, Germany

[21] Appl. No.: 415,974

[22] Filed: Apr. 3, 1995

[30] Foreign Application Priority Data

Apr. 27, 1994 [DE] Germany .................. 44 15 556.5

[51] Int. Cl.[6] ........................................ C07F 7/08
[52] U.S. Cl. .................. 556/445; 556/428; 556/443; 556/444; 556/449; 252/351; 252/353; 252/355
[58] Field of Search .................... 556/443, 444, 556/449, 445, 428; 252/351, 353, 355

[56] References Cited

U.S. PATENT DOCUMENTS

| 3,355,473 | 11/1967 | Clark et al. | 556/449 |
| 3,381,019 | 4/1968 | Morehouse | 556/445 |
| 3,538,137 | 11/1970 | Viventi | 556/445 |
| 4,839,443 | 6/1989 | Akutsu et al. | 556/449 X |

OTHER PUBLICATIONS

Chemie und Eigenschaften von Glycerinethersulfaten by B. Gruber, B. Fabry B. Giesen, R. Miller & F. Wangemann, 1993, (pp. 422–426).

*Primary Examiner*—Paul F. Shaver
*Attorney, Agent, or Firm*—Anderson Kill Olick & Oshinsky

[57] ABSTRACT

The invention relates to novel organosilyl and organosiloxanyl derivatives of glycerin ethers of the general formula

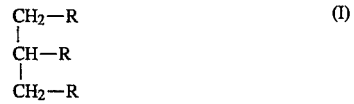

wherein
R represents —OH or the —OCH$_2$—CH=CH—(CH$_2$)$_3$—CH=CH$_2$ group or the —(R$^5$)$_a$—R$^6$ group or the —OCH$_2$—CH=CH—(CH$_2$)$_5$—R$_4$ group.

8 Claims, No Drawings

ORGANOSILYL AND ORGANOSILOXANYL DERIVATIVES OF GLYCERIN ETHERS AND THEIR USE

FIELD OF INVENTION

The invention relates to novel organosilyl and organosiloxanyl derivatives of glycerin ethers. The invention further relates to surfactants in aqueous media comprising an effective amount of the inventive organosilyl and organosiloxanyl derivatives.

OBJECT OF THE INVENTION

An object of the invention is the inventive organosilyl and organosiloxanyl derivatives of glycerin ethers. A further object of the invention is a surfactant in aqueous media comprising an effective amount of the inventive organosilyl and organosiloxanyl derivatives.

SUMMARY OF THE INVENTION

The inventive derivatives have the general formula

     (I)

wherein

R represents —OH, or the —OCH$_2$—CH=CH—(CH$_2$)$_3$—CH=CH$_2$ group, or the —(R$^5$)$_a$—R$^6$ group, or the —OCH$_2$—CH=CH—(CH$_2$)$_5$—R$_4$ group, with the proviso that at least one of the R groups has the last-mentioned meaning, R$^4$ being a silyl group having the formula —SiR$^1$R$^2$R$^3$, in which R$^1$, R$^2$ and R$^3$ are the same or different aliphatic or aromatic hydrocarbon groups, or a linear or branched organosiloxanyl group with 2 to 200 silicon atoms, R$^5$ is a group having the formula -O(CH$_2$)$_b$— or a polyether group having the formula —(OC$_n$H$_{2n}$)$_c$, wherein b has a value of 1 to 11, n has an average value of 2 to 2.5 and c a value of 1 to 21, R$^6$ is an —OSO$_3$X or —OR$^7$ group, wherein X is hydrogen, alkali or an optionally substituted ammonium ion and R$^7$ is a hydrogen group, an alkyl group with 1 to 4 carbon atoms or an acetyl group, and a is 0 or 1, and is 1 in the event that R$^6$ is the —OR$^7$ group.

Preferably, R$^1$, R$^2$ and R$^3$ or the organic groups of the polysiloxane are alkyl groups with 1 to 4 carbon atoms and one of these groups can be replaced by a phenyl group. Particularly preferred are compounds, in which at least 90% of the R$^1$, R$^2$ and R$^3$ groups or the organic group of the polysiloxane are methyl groups.

The inventive organosilyl or organosiloxanyl derivatives are easily accessible by way of the glycerin octadienyl ethers, which are obtained by telomerizing butadiene with glycerin (Gruber et al., "Chemistry and Properties of Glycerin Ether Sulfates", Tenside Surf Det., 30, (1993), 6).

They can be synthesized easily by means of an addition reaction between silanes of the general formula

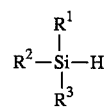

or hydrogensiloxanes and glycerin octadienyl ethers of the general formula

wherein R is —OH or the —OCH$_2$—CH=CH—(CH$_2$)$_3$—CH=CH$_2$ group, in the presence of a known hydrosilylation catalyst.

In the event that triethers are used as starting material, compounds of the following general formulas

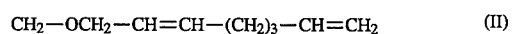     (II)

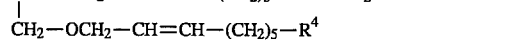     (III)

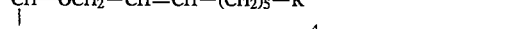     (IV)

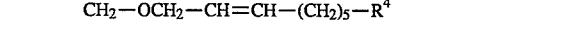

or their stereoisomers are thus obtained, wherein R$^4$ has the meaning given above.

The above compounds, particularly those with a single silyl or siloxyl group (formula II), can be used as modifiers for curable resins, such as organopolysiloxane acrylates, since this novel class of substances combines the properties of pure organosilicon compounds in an advantageous manner with those of compounds having strictly a hydrocarbon backbone.

Particularly when used in polymer preparations that consist of two or more polymers of different types, these modifiers act as compatibilizers.

In the case that monoethers or diethers are used as starting compound, compounds of the general formula

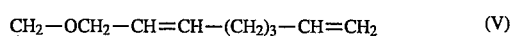     (V)

or

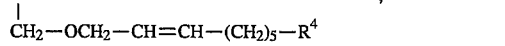     (VI)

or their stereoisomers are obtained.

Compounds of formula V can also be used over the existing double bond for modifying the properties of curable resins.

Moreover, the olefinic double bond permits this class of substances to be used in standard reactions of organic chemistry, such as sulfonations, epoxidations, metatheses, brominations, conversions into Bunte salts, etc.

Because of the OH groups, both groups of compounds can also be used as monohydric or dihydric components for modifying polyester or polyurethane resins.

The compounds of formulas V and VI are particularly suitable for being reacted further to surfactant compounds of the general formulas

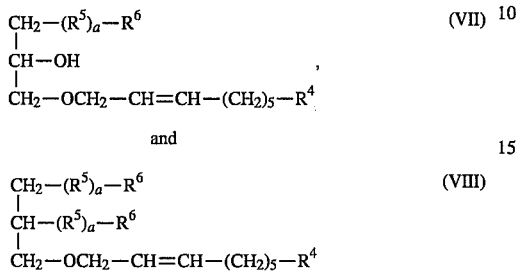

wherein $R^5$ and $R^6$ have the meaning given above.

The $-(R^5)_a-R^6$ group should be selected by a suitable adjustment of the HLB value so that the resulting compounds have a high degree of compatibility with the target medium. For aqueous media, for example, the HLB should be adjusted to a value greater than 5 by incorporating suitable hydrophilic groups.

Preferably, $R^5$ is a polyether group having the formula $-(OC_nH_{2n})_c-$, in which n preferably has a value of 2.0, so that in this case all oxyalkylene units are present as oxyethylene units. Subscript c preferably is 3 to 6.

The compounds of formulas VII and VIII can be synthesized by known methods by etherifying or alkoxylating the compounds of formulas VI and VII or by sulfonating or sulfating the hydroxyl group, directly linked to the glycidyl group. The hydroxy-functional polyethers, which result from the etherification or alkoxylation, can be sulfated subsequently. The group, joined on during the sulfation, is the $-OSO_3X$ group, wherein X is hydrogen, alkali or an optionally substituted ammonium ion.

Examples of the inventive organosilyl or organosiloxanyl derivatives of glycerin ethers with surfactant character are

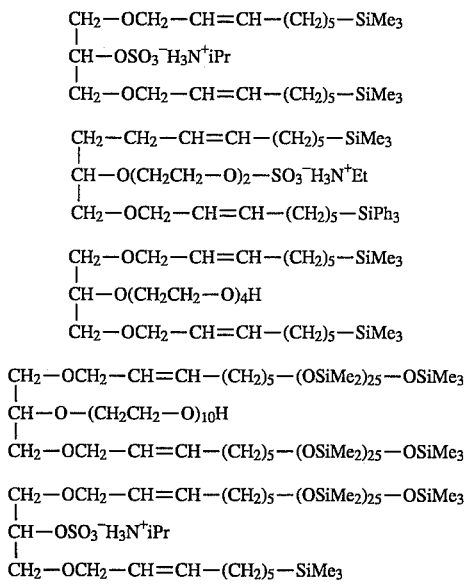

A further object of the invention is the surfactants in aqueous media comprising the effective amount of the compounds of the general formulas VII and VIII. Important utilizations of the compounds as surfactants are:

- as wetting agent: in preparations for treating plants (agricultural formulations); for improving the wetting of low surface energy substrates, such as polyethylene and polypropylene surfaces, for use in the paint industry; in the manufacture of photographic films; in electroplating;
- as dispersant for dispersion paints, pigments and fillers;
- as emulsifiers or additives in the textile industry for producing textile auxiliaries, finishes, lubricants and antistatic preparations; as dyeing aids;
- as surfactants in general: for use in fire extinguishers, as foam stabilizers; as surface active additives in high-speed printing inks, adhesives, dispersion adhesives, melt adhesives; for use in detergents; as additives for industrial cleaners;
- as raw materials for use in cosmetics, such as in personal care products, shampoos, shower baths;
- in industrial applications and in the household: as anti-fogging agents; for use in dish-rinsing detergents, laundry detergents, toilet cleaners, self-gloss emulsions.

In this connection, the incorporation of organosilane and, particularly, of trimethylsilane groups, provides, contrary to structures with immanent siloxane substitution at the glycerin backbone, the option of achieving biologically degradable surfactants.

EXAMPLE 1

Addition Reaction Between Trimethylsilane and Glycerin Monooctadienyl Ether

Into a 300 mL laboratory autoclave, 35.0 g (0.175 moles) of glycerin monooctadienyl ether, 0.5 g of sodium carbonate and 3 mg of cis-(diamino)dichloroplatinum are weighed. In an inert atmosphere of argon, the autoclave and contents are cooled in an acetone/dry ice bath and 13.6 g (0.184 moles) of trimethylsilane, with a boiling point of 6.7° C. are siphoned over from the condensed phase. The autoclave is closed and heated to 130° C. At the same time, the internal pressure increases to 12.3 bar, only to fall once again then to 4.5 bar, which indicates a reaction.

After the autoclave is cooled to room temperature and the pressure in the autoclave is relieved, the contents, weighing 46.5 g (this indicates a mass loss of 1.5 g) are freed from platinum catalyst by filtration.

Hydroxyl number: 409 (theoretical), 385 (actual)

The $^{29}$Si-NMR and $^1$H-NMR spectroscopic analyses reveals the following structure for the product:

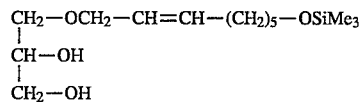

The product is freed from volatile components at 50° C. under the vacuum of an oil pump and then used without further preparation for the ethoxylation.

EXAMPLE 2

Use of the Addition-Reaction Product Obtained in Example 1 for Ethoxylation

To a 3-neck flask, which is equipped with an intensive condenser, thermometer, dropping funnel provided with a cooling mantle and a nitrogen connection, 40 g (0.145 moles) of the addition-reaction product of Example 1 and 1 g of a 50% boron trifluoride etherate solution are added. After that, 56.5 g (1.28 moles) of condensed ethylene oxide is slowly added dropwise. The exothermic reaction is counteracted by using an ice bath, so that the internal temperature does not exceed 20° to 30° C. After that, stirring is continued for a further 2 hours at room temperature and the reaction solution is neutralized with 2 g of sodium hydrogen carbonate and 1 g of water (1% by weight). Subsequently, the volatile components are removed from the product at 90° C. under the vacuum of a water-jet pump.

The subsequent filtration after prior addition of filter aid "Celite J 10" results in a clear product, which is slightly colored yellow and, according to $^1$H-NMR spectroscopy as well as GPC, has 4 units of oxyalkylene and, accordingly, can be reproduced by the following average formula:

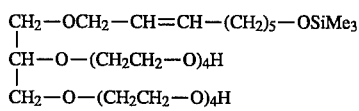

EXAMPLE 3

Synthesis of the Product of the Addition Reaction Between Glycerin Dioctadienyl Ether and Two Equivalents of Heptamethyltrisiloxane To a 500 mL 4-neck flask with KPG stirrer and reflux condenser, 70 g (0.23 moles) of glycerin dioctadienyl ether together with 10 mg of cis-diaminoplatinum dichloride are added with stirring and heated to 100° C. Heptamethyltrisiloxane (102 g, 0.46 moles) is successively added dropwise. At the end of the addition (about 1 hour), stirring is continued for a further 2 hours at 120° C. After the reaction batch has cooled down, catalyst is removed by means of a filter press.

A readily mobile, colorless oil (165 g) is obtained, the structure of which was characterized by $^1$H-NMR as follows:

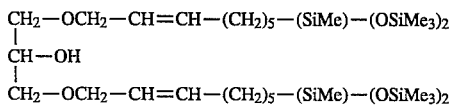

EXAMPLE 4

Use of the Product Obtained in Example 3 for Synthesizing its Isopropylammoniumsulfato Derivative To a 500 mL 4-neck flask, equipped with stirrer, reflux condenser, thermometer and dropping funnel, 150 g (0.20 moles) of the addition-reaction product from Example 3, 20.4 g (0.21 moles) of freshly ground (mortar and pestle) amidosulfuric acid and 20 g of dimethylformamide are mixed under a blanket of nitrogen and heated for 4 hours to an internal temperature of 85° C. The reaction mixture is thereupon mixed at room temperature with 14.2 g (0.24 moles) of i-propylamine, the temperature of the mixture increasing and ammonia gas escaping. By these means, acid groups present in the product are neutralized at the same time. After that, the product is filtered and then freed from N,N-dimethylformamide and excess isopropylamine at 85° C. under the vacuum of an oil pump.

A highly viscous, yellowish oil (174 g) is obtained.

The integration relationship in the $^1$H-NMR spectrum confirms a degree of sulfation of 85% and assigns the following structure to the product:

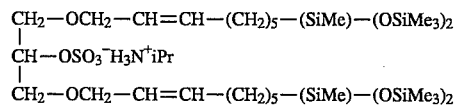

We claim:

1. Organosilyl and organosiloxanyl derivatives of glycerin ethers of the general formula

wherein

R represents —OH, —OCH$_2$—CH=CH—(CH$_2$)$_3$—CH=CH$_2$ group, —(R$^5$)$_a$—R$^6$ group or —OCH$_2$—CH=CH—(CH$_2$)$_5$—R$_4$ group, with the proviso that at least one of the R groups has the last-mentioned meaning, R$^4$ being a silyl group having the formula —SiR$^1$R$^2$R$^3$, in which R$^1$, R$^2$ and R$^3$ are the same or different aliphatic or aromatic hydrocarbon groups, or a linear or branched organosiloxanyl group with 2 to 200 silicon atoms, R$^5$ is a group having the formula —O(CH$_2$)$_b$— or a polyether group having the formula —(OC$_n$H$_{2n}$)$_c$, wherein b has a value of 1 to 11, n has an average value of 2 to 2.5 and c a value of 1 to 21, R$^6$ is an —OSO$_3$X or —OR$^7$ group, wherein X is hydrogen, alkali or an substituted ammonium ion which may be substituted and R$^7$ is a hydrogen group, an alkyl group with 1 to 4 carbon atoms, or an acetyl group, and a is 0 or 1, and is 1 in the event that R$^6$ is the —OR$^7$ group.

2. The organosilyl and organosiloxanyl derivatives of claim 1, wherein R$^1$, R$^2$ and R$^3$ and the organic groups of the polysiloxane are alkyl groups with 1 to 4 carbon atoms and one of these groups is a phenyl group.

3. The organosilyl and organosiloxanyl derivatives of claim 2, wherein at least 90% of the R$^1$, R$^2$ and R$^3$ groups and the organic groups of the polysiloxane are methyl groups.

4. The organosilyl and organosiloxanyl derivatives of claim 1 or 2, wherein one or two of the R groups represent the —(R$^5$)$_a$—R$^6$ group.

5. The organosilyl and organosiloxanyl derivatives of claim 4, wherein R$^5$ is a polyether group, in which n has a value of 2 and c a value of 3 to 6.

6. The organosilyl and organosiloxanyl derivatives of claim 4, wherein X is an alkylammonium group, the alkyl group of which has 1 to 10 carbon atoms.

7. The organosilyl and organosiloxanyl derivatives of claim 1 or 2, wherein two of the R groups represent the —OCH$_2$—CH=CH—(CH$_2$)$_3$—CH=CH$_2$ group.

8. A surfactant in aqueous media comprising an effective amount of the organosilyl and organosiloxanyl derivatives of the glycerin ethers of claims 4, 5 or 6.

* * * * *